United States Patent [19]

Rahlff

[11] Patent Number: 5,687,429

[45] Date of Patent: Nov. 18, 1997

[54] URINAL

[75] Inventor: Søren Rahlff, Nivå, Denmark

[73] Assignee: Jan Tholstrup, Tappernoje, Denmark

[21] Appl. No.: 448,581

[22] PCT Filed: Oct. 10, 1994

[86] PCT No.: PCT/DK94/00377

§ 371 Date: Jul. 14, 1995

§ 102(e) Date: Jul. 14, 1995

[87] PCT Pub. No.: WO95/10250

PCT Pub. Date: Apr. 20, 1995

[30] Foreign Application Priority Data

Oct. 8, 1993 [DK] Denmark ................. 1128/93

[51] Int. Cl.$^6$ ............................................. A47K 11/00
[52] U.S. Cl. ................................................... 4/144.4
[58] Field of Search ........................... 4/144.3, 144.4; 128/761; 604/329

[56] References Cited

U.S. PATENT DOCUMENTS

| 1,510,973 | 10/1924 | Behan . |
| 3,963,020 | 6/1976 | Hall . |
| 4,496,355 | 1/1985 | Hall et al. . |
| 4,528,703 | 7/1985 | Kraus . |
| 4,911,698 | 3/1990 | Wapner . |
| 5,004,463 | 4/1991 | Nigay ................. 4/144.3 X |
| 5,387,205 | 2/1995 | Cummins ................. 604/329 |

FOREIGN PATENT DOCUMENTS

| 23942 | 2/1981 | European Pat. Off. . |
| 2082679 | 12/1971 | France . |
| 2624004 | 6/1989 | France . |
| 2126902 | 9/1982 | United Kingdom . |
| 90/08561 | 8/1990 | WIPO . |

Primary Examiner—Charles E. Phillips
Attorney, Agent, or Firm—Birch, Stewart, Kolasch & Birch

[57] ABSTRACT

A urinal for women having an elongated inlet member to be inserted between the labia majora of the woman. The inlet member comprises an inlet opening with a periphery which forms a complete or partial seal around the female urethral orifice during use. The inlet member further comprises a flow duct between the inlet opening and the outlet opening delimited by a front and rear wall as well as by a right and left lateral wall, where the lateral walls are preferably arranged symmetrically around a longitudinal plane of symmetry. Furthermore, the inlet member is sealingly connected to a collecting container such as a bag at the outlet opening, so that the liquid can pass through the flow duct and into the collecting container. The external surfaces of the lateral walls diverge in a direction away from the inlet opening at least in an area directly around the periphery of the inlet opening. Such a urinal, which is particularly developed for non-portable use, does not require substantial parting of a woman's legs when positioning the urinal and it ensures sealed contact.

20 Claims, 2 Drawing Sheets

URINAL

TECHNICAL FIELD

The present invention relates to a urinal for women having an elongated inlet member to be inserted between the labia majora of the women.

BACKGROUND ART

Portable urinals in various embodiments have been known for some time, and have mainly been developed for women suffering from urinary incontinence. A second type of urinal is for occasional use only, eg. for bedridden patients or immobilized non-incontinent women.

EP patent application no. 23 942, U.S. Pat. No. 4,495,355 and PCT publication no. 90/08561 disclose urinals to be used by women suffering from incontinence comprising an inlet member, a tubular section and a container. The inlet member comprises a small, oval, cup-shaped or gourd-shaped unit to be inserted between the labia majora of the wearer so that the unit will be completely surrounded by the labia majora. The unit is provided with a shallow recess or opening facing the female urethra. Opposite this opening the unit is provided with an outlet leading to a container. When a woman urinates, the urine rum first into the recess, through the tube and then into the collecting member. Since the recess is very small and the outlet tube is very narrow, urine easily collects in the recess. This causes overpressure in the recess so that urine flows over the edges rather than into the outlet tube into the collector. These incontinence devices are therefore suitable only for collecting small amounts of urine. If a woman intends to empty her bladder completely with the help of such a device, there is a considerable overflow risk. Devices of the above-mentioned type are also difficult to insert in the correct position.

A second type of urinals is described in FR patent application no. 2,624,004, EP patent application 314,578, GB patent application no. 2,126,902 and U.S. Pat. No. 4,528,703. These urinals are also provided with an inlet member and an outlet tube leading to a collecting container or the like. This second type of urinals differs from the first by the inlet member not completely surrounded by the labia majora when the urinal is correctly positioned. The urinals disclosed in the tint three patent specifications are thus provided with an inlet member having an outer portion for surrounding the labia majora and an internal projecting portion for surrounding the female urethral orifice between the labia majora. The urinal disclosed in U.S. Pat. No. 4,528,703 has a cup-shaped receiving member to be inserted between the female labia majora, the front part of said cup-shaped member narrowing to form a comparatively rigid tubular section which may be connected to a container. This type of urinal is primarily intended to be used by women suffering from incontinence who cannot easily collect large mounts of urine at a time. Several of the urinals mentioned above, especially the last one, are practically unusable when the woman is lying on her back.

In order to facilitate the positioning the two types of urinals described above, the inner part of the inlet member may be provided with a projecting part to be inserted into the vagina. This often causes discomfort to the wearer and may easily result in urine running into the vagina, which is unacceptable for hygienic reasons. In order to find the correct position for the urinal, a woman has to use both hands. That is why immobilized women often have to ask for help from another person for inserting the urinal. Inserting the types of urinals described above requires a woman to part her legs at a relatively wide angle. Then the woman, or a helper, has to part the labia majora with one hand and positioned the inlet member of the urinal with the other hand so that it covers the urethral orifice. It is frequently necessary to confirm the correct position of the inlet member around the urethra by means of a finger.

U.S. Pat. No. 3,963,020 discloses a non-portable urinal to be used by bedridden or immobilized women. This urinal comprises an inlet member and a collecting member. The inlet member is the upper portion of the collecting member comprising two cup-like pans which form a spout. Prior to use one cup-shaped part of this urinal is inserted into the vagina, resulting in the second cup-shaped part covering the urethral orifice within the labia majora. As mentioned above this is not a very suitable arrangement, which may cause the woman considerable discomfort. Moreover, the woman is again forced to use both hands to insert the urinal correctly.

SUMMARY OF THE INVENTION

It is the object of the present invention to provide a urinal, preferably for non-portable use, which does not require substantial parting of a woman's legs when positioning the urinal and which is ensured sealed contact.

The object of the invention is accomplished by a urinal for a woman comprising an elongated inlet member to be inserted between the labia majora of the woman, and having first and second lateral walls and first and second end walls, said walls defining therebetween a flow duct extending between an inlet opening and an outlet opening, the latter being adapted to be connected to a urine collecting container, the lateral side walls having opposite external side surfaces, which at least closely adjacent to the inlet opening diverge from the inlet opening towards the outlet opening, a longitudinal extension of the inlet member connected to the first end wall thereof forming a handle, the second end wall and at least adjacent parts of the first and second side walls defining close to the inlet opening a sealing surface for sealing engagement with labia minora of a woman, whereby she may grip the handle and position and hold the inlet member in proper engagement with her labia majora and minora while she is urinating.

A urinal according to the invention can thus be positioned by a woman, regardless of whether she is standing, sitting or lying. A urinal according to the invention may be put into place with one hand without the legs having to be particularly parted.

The outer lateral walls of the inventive urinal's inlet member are easily positioned between the female labia majora, since the divergent external surfaces are contacting the inner sides of the female labia majors substantially over the entire length of said surfaces when the urinal is in use. Thus the force the inlet member exerts on the labia majora to split them and/or keep them split after inserting the urinal is substantially evenly distributed over the entire contact area between the inner sides of the female labia majors and the external surfaces of the lateral walls.

As a result, the urinal according to the invention is much more comfortable to use than previously known devices.

Moreover, because of the divergent external surfaces of the lateral walls the risk of spilling urine during use is minimal, since the urinal according to the invention is supported by the labia majora when the inlet member is placed between them. As a result the risk of the inlet member being displaced or moved out of the correct position is minimized.

It is of particular importance that the external surfaces of the lateral walls diverge in an area directly round the periphery of the inlet opening. The external surfaces of the lateral walls may advantageously diverge over their entire length.

The degree of divergence exhibited by the external surfaces of the lateral walls at any given point in a cross-section at right angles to the plane of symmetry and said surfaces may advantageously be described as angle $\alpha(x)$ between the transverse tangent (parallel to the cross-sectional plane) to a point at a distance x from the periphery of the inlet opening and the center plane.

For each point of a cross-section at right angles to the plane of symmetry, the degree of divergence exhibited by the external surfaces of the lateral walls at the periphery of the inlet opening is in the following given as the angle between the transverse tangent to said point and the plane of symmetry, i.e. $\alpha=\alpha(x)$, where x is infinitesimally small.

$\alpha$ is preferably wider than 10°, advantageously between 20° and 60° and particularly between 30° and 55°.

The external surfaces of the lateral walls are preferably curved, i.e. angle $\alpha(x)$ decreases with increasing distance x from the periphery of the inlet opening.

When x is between 0.2 and 1.0 cm, $\alpha(x)$ is preferably between 15° and 45°, and particularly between 20° and 40°.

The internal surfaces of the urinal's walls may advantageously diverge from the inlet opening to the outlet opening so that the flow member is shaped like a reversed funnel. During use the urine runs quickly away from the vagina into the collecting container substantially avoiding urine spraying backwards, even if the stream is ejected under comparatively high pressure.

The inlet opening may by circular or elongated. Preferably the inlet opening is elongated, extending along the same longitudinal axis as the inlet member, and has a length from the front end wall to the rear end wall of between 3 and 10 cm, particularly 5 to 7 cm.

The inlet opening is advantageously most narrow in an area close to the from end wall and widest in an area 0.2 to 3 cm in longitudinal direction away from the rear end wall. Thus the inlet opening is pear-shaped, having a maximum width of preferably 2 to 3 cm.

The shape of the opening resembles substantially the contour of the labia minora. When the periphery of the opening or the area around it contact the labia minora, an excellent seal is achieved. It is unnecessary for the periphery of the opening to exactly follow the contour of the labia minora, since the seal between labia and inlet opening can be provided by the area round the periphery at the front and rear end wall.

It is equally unnecessary for the periphery of the opening or the surrounding area to fit tightly against the urethral orifice over its entire circular extension. If the opening is elongated and has a length of the preferred dimensions as described above, it is obvious that the periphery at the front end wall not necessarily is in sealing contact with the female sexual organs.

In a preferred embodiment of the invention the periphery of the inlet opening has a variable distance to a substantially horizontal plane which is at right angles to the plane of symmetry and in alignment with the periphery at the two end walls. Thus the distance between the two end walls increases towards the widest section of the inlet opening.

The degree of divergence exhibited by the outer lateral walls at the periphery of the opening may advantageously vary along the periphery. In other words, angles $\alpha$ vary in relation to the cross-section where an angle is measured.

In a particularly advantageous embodiment, $\alpha$ decreases with increasing distance between the cross-section and the widest section of the inlet opening.

The periphery of the inlet opening is preferably provided with a relatively non-cutting, sharp edge thus permitting sealing contact with the female labia minora, when the urinal is positioned ready for use.

Advantageously, the part of the rear end wall's external surface closest to the inlet opening, in the following called upper part, is substantially in the same plane as the horizontal plane in alignment with the periphery of the inlet opening at the two end walls and at right angles to the plane of symmetry, thereby forming a bulb. The upper part of the rear end wall's external surface, also called bulb's length, has a length of preferably 0.5 to 2 cm, seen in the longitudinal direction of the inlet member.

The bulb functions in two ways: It acts as a trap for urine preventing this liquid to spray or run back to the female sexual organs. The bulb makes it easier to position the urinal, as it is placed at the point where the labia minora meet.

There are no requirements concerning a precise border between the surfaces of the inlet member and the end walls.

The front and rear end walls are therefore preferably curved walls connecting the two end walls with a preferred radius of the curvature of between 1 and 5 mm, especially 2 and 10 mm. If desired, the radius may vary as a function of the variable distance from the periphery of the inlet opening.

The thickness of the lateral walls may either be the same over their entire lengths or vary. In a preferred embodiment the wall thickness increases with increasing distance from the inlet opening.

The lateral walls may be provided with a slot or cutout so that one lateral wall, in a cross-sectional view, looks like an inclined, reversed V with the peak being the periphery of the inlet opening. The purpose of the cutout is to save material.

The inlet member is advantageously provided with a handle, preferably an extension of the front end wall leading away from the inlet opening in its longitudinal direction.

The inlet member may be made from any non-toxic material being reasonably resistant to urine such as cardboard or polymeric materials. When choosing either the material or the thickness, the inlet member must substantially be able to keep its form during use. Suitable materials are for instance thermoplastic elastomers, including comparatively inexpensive polyolefins such as polyethylene or polypropylene, polyurethane, ethylene vinyl acetate, polystyrene and polyvinyl chloride. The preferred embodiment makes use of foam materials such as foamed polyurethane or polystyrene. It is particularly preferred to use materials such as foamed polyurethane or polystyrene and particularly preferred to use materials that can be injection-moulded.

Moreover, the container and, if desired, the pipe or tube section may be made of any non-toxic material having a reasonable resistance to urine.

Advantageously the materials for the inlet member and the container or the pipe or tube section are chosen with respect to their ability to be glued, welded or fastened to each other in another way.

The inlet member may, as mentioned above, form the inlet to a tube or pipe section which may be fixed in a manner known per se to a container or the like. Alternatively the inlet member may form, and that is the preferred embodiment, an inlet directly into the container. Thus the urinal does preferably not pass through substantially narrow passages at the inlet into the container.

The container may be rigid or compressible. If the container is rigid, either the container or the inlet member is advantageously provided with a vent to allow air to pass out of the container. Such a vent is preferably provided with a collector for liquids. In a particularly preferred embodiment the container is a compressible bag.

In a particularly preferred embodiment, the container is a compressible bag comprising two sheets welded together or glued together along their periphery, one sheet having an opening corresponding to the outlet opening in the inlet member. The area surrounding the outlet opening is fixed to the area surrounding the sheet's opening.

The inlet of the container may be provided with a liquid flap known from bags for patients suffering from urine incontinence. The container may also contain components absorbing liquids and/or air, optionally in the form of a granulate. Such components are generally known to people skilled in the art.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is disclosed in greater detail below and with reference to the accompanying drawings which are given by way of illustration only, and thus are not limitative of the present invention, and in which:

FIG. 1 is a perspective view of a preferred embodiment of the inlet member of the urinal according to the invention;

FIG. 2 is a view of the inlet member of FIG. 1 seen from the inlet side;

FIG. 3 is a view of the inlet member of FIG. 1 seen from the outlet member;

FIG. 4 is a sectional view of the inlet member of FIG. 2 along the line IV—IV;

FIG. 5 is a sectional view of the inlet member of FIG. 2 along the line V—V; and FIG. 6 is a rear view of the inlet member.

DETAILED DESCRIPTION OF THE PREFERRED EMBODIMENTS

Figure 1:
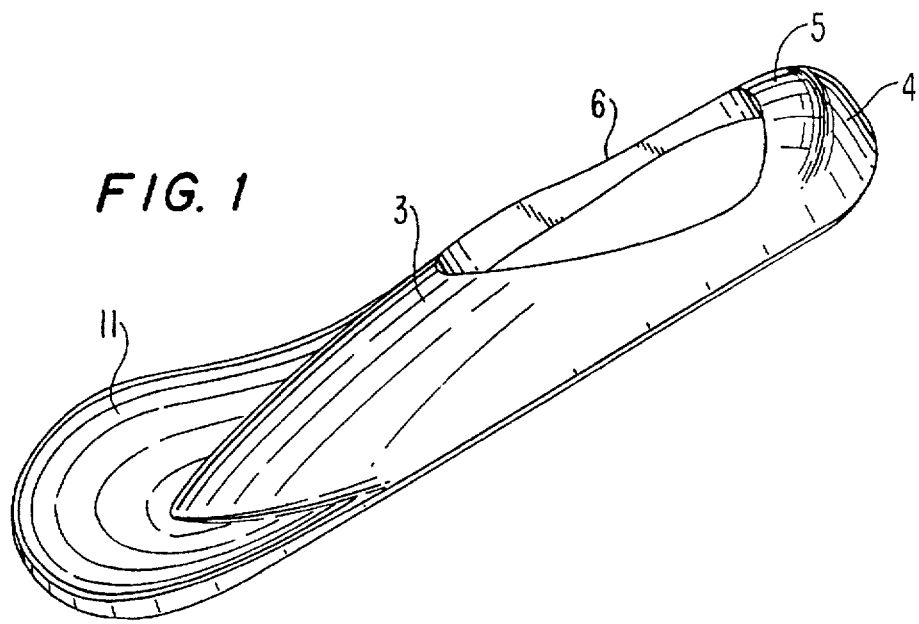
FIGS. 1–6 are views of a preferred embodiment of the invention.

The inlet member is elongated in a plane of symmetry yy' and has a left and a right lateral wall 1, 2 with external surfaces 1a, 2a and internal surfaces 1b and 2b as well as a front end wall 3 and a rear end wall 4 with external surfaces 3a, 4a and internal surfaces 3b, 4b.

The inlet member is provided with an inlet opening 7 and an outlet opening 8. Both openings are delimited by the lateral and end walls 1, 2, 3, 4.

The inlet opening is pear-shaped with a periphery 6 which at least at the end closest to the rear end wall 4 sealingly contacts the female urethral orifice during use. The external surfaces 1a, 2a of the lateral walls are curved and diverge away from the inlet opening 7.

The degree of divergence exhibited by the external surfaces 1a, 1b of the lateral walls at a point on the external surfaces in a given cross-section and at a distance x from the inlet opening is described as angle α(x) in the correct plane of symmetry yy' and a transverse tangent to the point.

Figure 2:
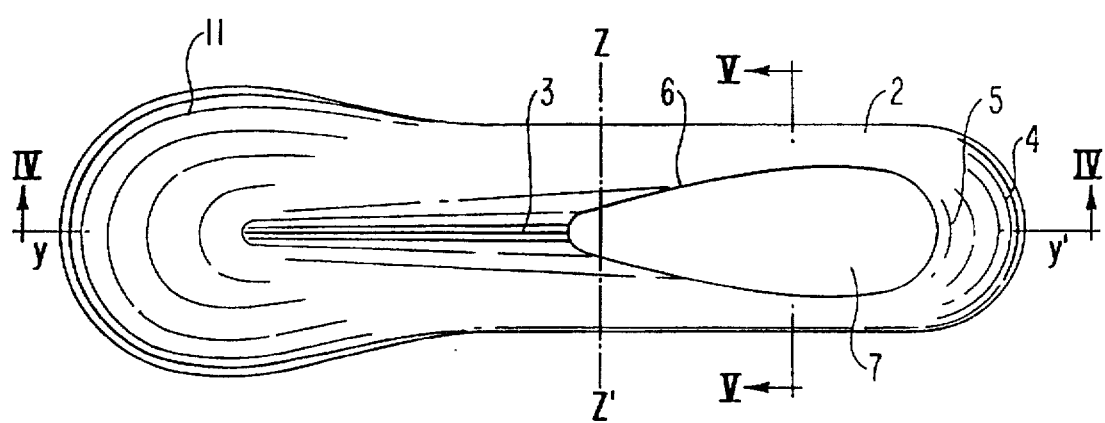
Figure 3:
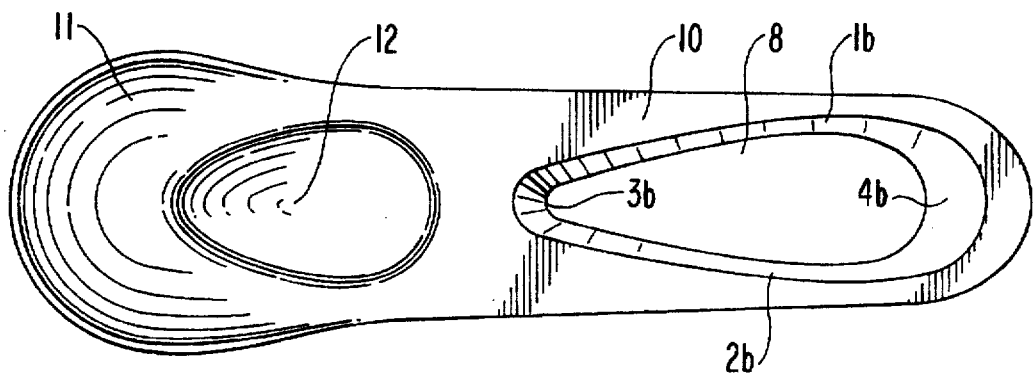
Figure 5:
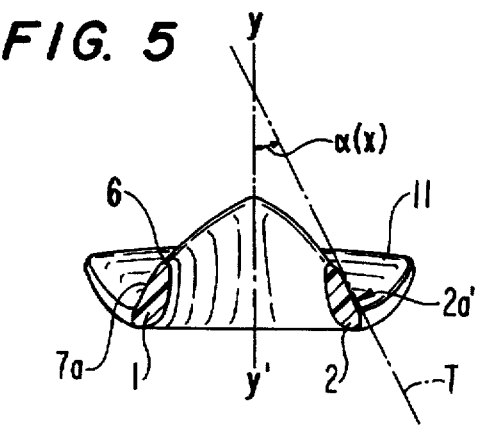

FIG. 5 depicts how the degree of divergence is measured at a point 2a' in a cross-section corresponding to section V—V and at a distance x from the inlet opening. The angle α(x) at 2a' is thus the angle between the transverse tangent T at the intersection with the axis of symmetry yy'. As is apparent from FIG. 5, α(x) changes in a given cross section by the value of x in such a way that α(x) decreases with increasing x. α(x) for a given x on the other hand changes with the selected cross-section. In the preferred embodiment α(x) for a given x is largest for a cross-section in the area where the inlet opening is widest, i.e. at the section V—V. The angle α(x) for a given x is thus larger for a cross-section along the line V—V than for a cross-section along the line zz', cf. FIG. 2, cutting through the opening in a narrower area.

A flow duct 13 is provided between the inlet opening 7 and the outlet member 8 delimited by the lateral walls and surfaces 1b, 2b, 3b, 4b of the front and rear walls. These surfaces thus constitute the wall surfaces of the flow duct. The wall surfaces 1b, 2b, 3b, 4b of the flow duct diverge in a direction away from the inlet opening 7 to the outlet member 8.

Figure 4:
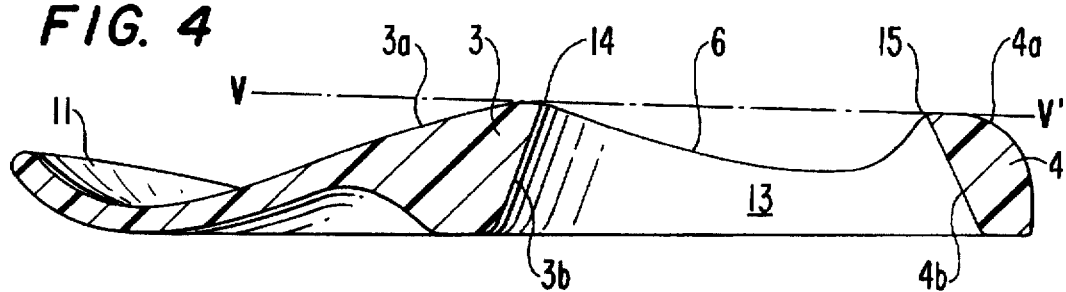

FIG. 4 shows that the distance of the periphery 6 of the inlet opening to a plane vv' decreases towards the widest section of the inlet opening.

The plane vv' is substantially horizontal and positioned in such a way that it is at right angles to the plane of symmetry and in alignment with two peripheral points 14, 15 intersected by the plane of symmetry yy'.

The thickness of the lateral walls increases with the distance from the inlet opening so that the bottom surface 10 surrounding the outlet member is provided with a certain width which can be glued to the collecting container.

The rear end wall 4 forms a bulb 5. The external surface 4a of the end wall is conceived such that the portion closest to the inlet opening coincides with the plane vv'.

As is apparent there is no defined border between the lateral walls and the end walls, as the end walls are curvatures connecting the lateral walls with each other.

The inlet member is also provided with a handle 11 as an extension of the front end wall 3. For material-saving purposes the front end wall is provided with a cutout 12.

Figure 6:
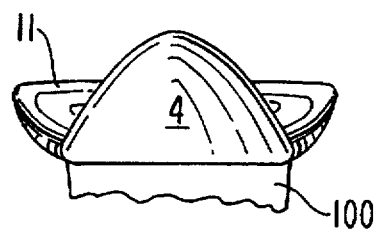

The inlet member is fixed to the collecting container in such a way that the handle is accessible. The collecting container 100 schematically shown in FIG. 6 for reasons of clarity is a compressible bag made of two sheets welded together along their periphery. One front sheet has an opening corresponding to the outlet opening of the inlet member with respect to size and shape. The bottom surface 10 of the inlet member is glued to the external surface of the bag in an area around the opening in the sheet.

When using the urinal a woman takes hold of the handle 11 with one hand and slightly parts her legs. Then the lateral walls 1, 2 of the inlet member are inserted between the labia majora wriggling the device slightly from side to side. If possible the woman may use her second hand to pan the labia majora. The bulb 5 is positioned where the labia minora meet. For the woman it is easy to determine whether the bulb is positioned correctly as this point forms a natural stop when pushing the inlet member slightly backwards. The periphery of the inlet member is now in sealing contact with the female urethral orifice in a circular extension from a point on one of the female labia minora further forward than the urethral orifice along said first labium minor to intersection with the second labium minor to a point on said second labium minor further forward than the urethral orifice. The woman can now urinate, whereupon the urinal is removed, emptied and either cleaned to be used again or thrown away.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. Urinal for a woman comprising an elongated inlet member to be inserted between the labia majora of a woman, said inlet member comprising an inlet opening with a periphery, the latter forming at least a partial seal around a female urethral orifice during use, said inlet member further comprising a flow duct between the inlet opening and an outlet opening delimited by a right and left lateral wall, said lateral walls preferably being arranged symmetrically around a longitudinal plane of symmetry, and by a front and rear wall, said inlet member furthermore being sealingly connected to a collecting container, at the outlet opening so that the liquid can pass through the flow duct and into the collecting container, external surfaces of the right and left lateral walls diverging in a direction away from the inlet opening at least in an area directly around the periphery of the inlet opening, the internal wall surfaces of the inlet member diverge in a direction from the inlet opening to the outlet opening, thus forming a reverse funnel.

2. A hand held urinal for a woman, the hand held urinal comprising an elongated inlet member to be inserted between the labia majora of the woman, and having first and second lateral walls and first and second end walls, said walls defining therebetween a flow duct extending between an inlet opening and an outlet opening, the latter being adapted to be connected to a urine collecting container, the lateral side walls having opposite external side surfaces, which at least closely adjacent to the inlet opening diverge from the inlet opening towards the outlet opening, a longitudinal extension of the inlet member connected to the first end wall thereof forming a handle, the second end wall and at least adjacent parts of the first and second side walls defining close to the inlet opening a sealing surface for sealing engagement with labia minora of a woman, wherein the internal wall surfaces of the inlet member defining the flow duct diverge in a direction from the inlet opening to the outlet opening so as to define a reverse funnel, whereby she may grip the handle and position and hold the inlet member in proper engagement with her labia majora and minora while she is urinating.

3. The urinal according to claim 2, wherein the thickness of the lateral walls increases with distance from the inlet opening.

4. The urinal according to claim 2, wherein a tangent to the external side surface of each lateral wall at the periphery of the inlet opening and any cross-section at right angles to a plane of symmetry forms an angle α with said plane of symmetry which is larger than 10°.

5. The urinal according to claim 4, wherein the angle α decreases with decreasing distance between said any cross-section and the cross section where the width of the inlet opening attains it maximum.

6. The urinal according to claim 4, wherein the angle α is between 20° and 60°.

7. The urinal according to claim 6, wherein the angle α is between 30° and 55°.

8. The urinal according to claim 2, wherein a tangent to the external side surface of each lateral wall in any cross-section at right angles to the plane of symmetry forms an angle α(x) with said plane, where x is the distance from the inlet opening, said angle decreasing with increasing distance x, the angle α(x) being between 15° and 45°, when 0.2 cm<x<1.0 cm.

9. The urinal according to claim 8, wherein the angle α(x) is between 20° and 55°.

10. The urinal according to claim 2, wherein the collecting container is a flexible bag comprising two sheets sealed together along their periphery, one sheet having an opening which corresponds to the outlet opening of the inlet member and an area surrounding the outlet opening being fastened to a corresponding area surrounding the opening of the sheet.

11. The urinal according to claim 2, wherein the inlet opening is elongated and extends in the longitudinal direction of the inlet member, the inlet opening having a length to 3–10 cm from the first end wall to the second end wall, the width of the inlet opening being minimum in an area closest to the first end wall and maximum in an area located between 0.2 and 3 cm from the second end wall.

12. The urinal according to claim 11, wherein the periphery of the inlet opening is spaced from a plane which is tangential to said periphery at the end walls opposite first and second end walls, and which is at right angles to a plane of symmetry, said spacing increasing towards the widest section of the inlet opening.

13. The urinal according to claim 11, wherein the periphery of the inlet opening is defined by a relatively sharp edge.

14. The urinal according to claim 11, wherein the length of the inlet opening is between 50–70 mm.

15. The urinal according to claim 11, wherein the maximum width is 20–30 mm.

16. The urinal according to claim 2, wherein the contour of the inlet opening is substantially complementary to the contour of the labia minora.

17. The urinal according to claim 2, wherein the second end wall is comprised of wall curvatures between the two lateral walls, each curvature's external surface having a curvature radius of 1–15mm.

18. The urinal according to claim 17, wherein the radius of curvature is 2–10 mm.

19. The urinal according to claim 2, wherein the second end wall forms a bulb comprising an external surface portion of the second end wall closest to the inlet opening and substantially parallel to a plane, which is tangential to the periphery of the inlet opening at the two end walls and at right angles with a plane of symmetry.

20. The urinal according to claim 19, wherein the dimension of the bulb in the longitudinal direction of the inlet member is 5–20 mm.

* * * * *